United States Patent [19]

Schaub et al.

[11] Patent Number: 4,895,742
[45] Date of Patent: Jan. 23, 1990

[54] CONVERTIBLE RECEPTACLE

[76] Inventors: Clemens B. Schaub, 400 W. Romana St., Pensacola, Fla. 32595; Susan S. Raisch, 53 Cloister Pl., Staten Island, N.Y. 10306

[21] Appl. No.: 223,192

[22] Filed: Jul. 22, 1988

[51] Int. Cl.$^4$ .................. B65D 30/10; B65D 33/06
[52] U.S. Cl. .................................. 428/35.5; 383/4; 383/6; 383/16; 428/131; 428/136; 428/542.8
[58] Field of Search .............. 383/4, 6, 16; 428/35.5, 428/131, 136, 542.8

[56] References Cited

U.S. PATENT DOCUMENTS

| 2,682,290 | 6/1954 | Ditlea | 383/4 |
| 2,781,811 | 2/1957 | Dilar et al. | 428/52 |
| 4,542,050 | 9/1985 | Gallant | 428/188 |
| 4,789,247 | 12/1988 | Schnoor | 383/4 |
| 4,794,029 | 12/1988 | Tennant et al. | 383/4 |

FOREIGN PATENT DOCUMENTS 0569902  6/1945  United Kingdom .................. 383/4

Primary Examiner—James J. Seidleck
Attorney, Agent, or Firm—Klein & Vibber

[57] ABSTRACT

A convertible receptacle has two layers of sheet material joined to each other at their peripheries. The upper layer is provided with a central opening such that when the upper layer is lifted, debris lying on the upper layer enters the opening into a space between the upper and lower layer.

Preferred embodiments of the receptacle include drawstring means for lifting the upper layer away from the lower layer, for closing the receptacle, and for transporting the receptacle carrying debris.

The invention can be applied as a table cloth, drop cloth, leaf bag, or sanitary disposal in medical applications. Moreover, the invention can be applied as a convertible bag, such as a combination beach bag/towel.

7 Claims, 2 Drawing Sheets 4,895,742

CONVERTIBLE RECEPTACLE

FIELD OF THE INVENTION

The invention relates to a convertible receptacle, illustrated as a disposable tablecloth which, when operated according to the invention, converts into a trash bag for rapid disposal of table remains.

BACKGROUND OF THE INVENTION

Disposable tablecloths are known in the art and have been widely accepted by consumers as appropriate for use at picnics, children's parties, and the like. In conjunction with disposable tablecloths, disposable plates, cups, and utensils are also often used. In such instances, at the conclusion of dining, all of the table remains, including the tablecloth can be simply disposed of as trash. However, with known disposable tablecloths, it is still necessary to clear the table of table remains in order to remove the tablecloth from the table for disposal. With known disposable tablecloths, it has been attempted to fold the tablecloth over the table remains to thereby dispose of the tablecloth and table remains simultaneously. Such an effort can result in substantial saving of time and labor and thereby add convenient to the use of disposable tablecloths and table utensils. However, the design of known disposable tablecloths is not readily adapted for an efficient use in this respect.

Disposable drop cloths are also known and are used, e.g. in covering surfaces to protect them from falling debris, such as plaster, wallpaper, or the like. Disposable drop cloth means are also used in medical applications for sanitary insulation and in gardening. As with disposable tablecloths, it would often be advantageous if there were a simple but reliable way to wrap the drop cloth around the debris for disposal.

The known disposable tablecloths and drop cloths generally comprise a rectangular or circular sheet of plastic, heavy paper, or the like. In folding such a tablecloth or drop cloth over table remains or other debris in order to rapidly dispose of same, there is a possibility that the cloth will not fully encompass all of the debris. Thus, when carrying the folded cloth, including debris, to a proper place for disposal, it is often the case that some of the debris will spill out from the folded package.

SUMMARY OF THE INVENTION

It is an object of the present invention to create a convertible receptacle which will lie flat for use as a drop cloth or table cloth or the like, but which is particularly suited for rapid disposal of both cloth and debris in an efficient way.

The inventive receptacle is, in many respects, similar to known disposable tablecloths and drop cloths, but that it comprises a double (upper and lower) layer of sheet material instead of a single layer. Moreover, one layer, the upper layer, is provided with a central opening for collecting debris. The upper layer is also preferably provided with lifting means such that, when disposing of debris collected on the surface of the upper layer, the upper layer with the opening is lifted from the lower layer causing the debris to empty into the opening and thereby into a space created between the two layers of the cloth.

BRIEF DESCRIPTION OF THE DRAWINGS

With these and other objects in view, which will become apparent in the following detailed description, the present invention, which is shown by example only, will be clearly understood in connection with the accompanying drawing, in which.

DESCRIPTION OF THE PREFERRED EMBODIMENTS

Figure 1:
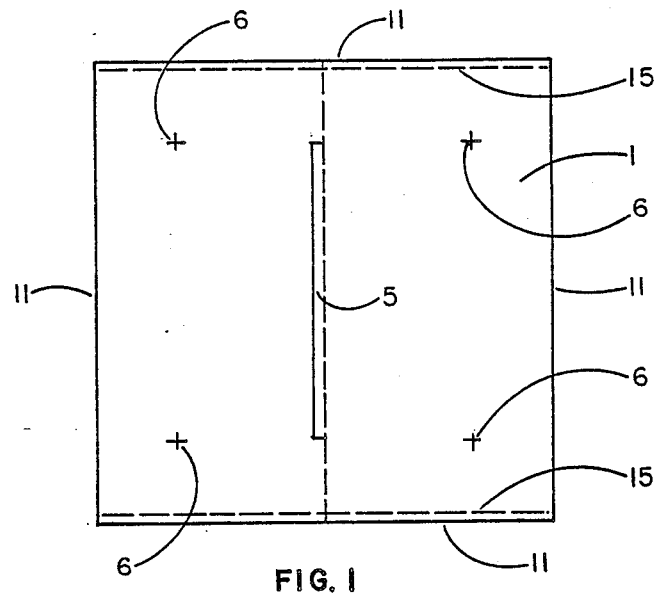
FIG. 1 is a plan view of an embodiment of the invention.
Figure 2:
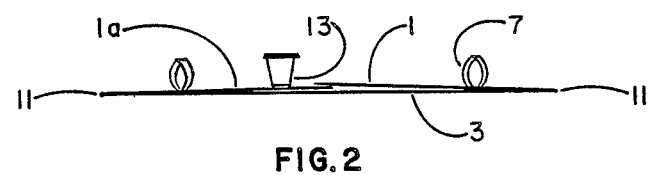
FIG. 2 is a side-sectional view of the embodiment of FIG. 1.
Figure 3:
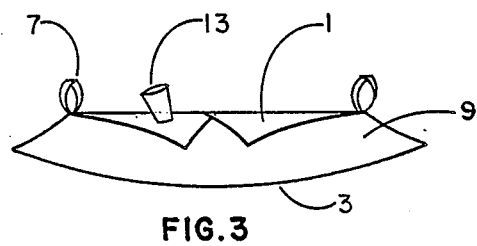
FIGS. 3 through 6 show the embodiment of FIGS. 1 and 2 in various stages of operation.
Figure 4:
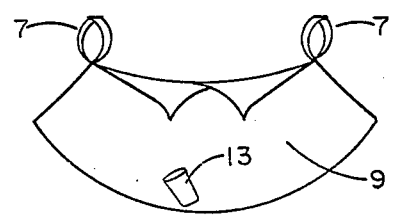
Figure 5:
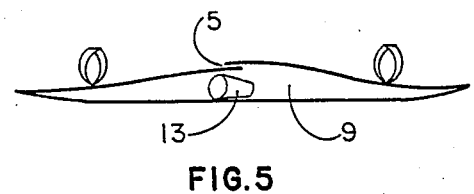
Figure 7:
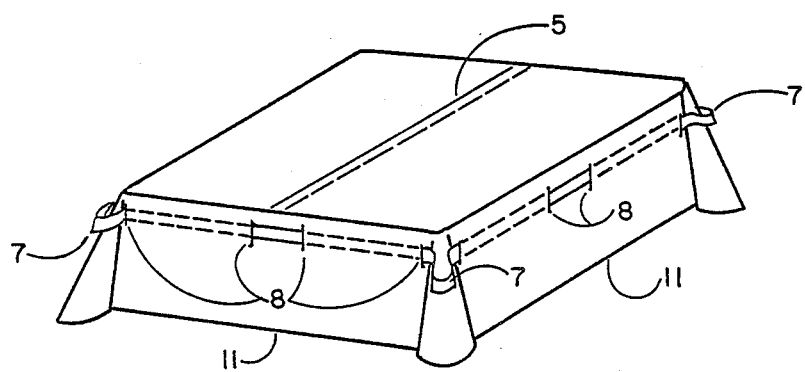
FIG. 7 is a perspective view of the invention functioning as a tablecloth.

Referring now to FIGS. 1 and 2, the inventive receptacle comprises two layers, an upper layer 1 and a lower layer 3, joined to each other at edges 11. The upper layer 1 is provided with a centrally located opening 5. In a preferred embodiment, this central opening 5 may be a slit closed with a lap as shown in FIGS. 2, 5 and 7. However, any operational opening may be used in order to achieve the desired effects as more fully described herein. This configuration may be obtained in several ways. For example, a cylindrical piece of sheet material can be extruded, flattened, sealed at its edges (e.g. 15 in FIG. 1), and provided with a slot 5, as can be gleaned from FIG. 1. Alternatively, three pieces of sheet material can be joined together at edges to form a two part upper layer 1, 1a, and a lower layer 3, whereby a lap covers opening 5 as shown in FIG. 2. Other methods of construction may be used so long as the upper layer 1 and lower layer 3 are joined to form a space 9 (FIGS. 3–5), accessible via opening 5.

The drawings show the inventive receptacle as a tablecloth in rectangular form. However, circular, triangular, or any other geometric shape may also used within the scope of this invention.

In order to make the most efficient use of the invention, it is most desirable to provide lifting means 7 which are attached to top layer 1. As shown in FIGS. 2 through 6 and in FIG. 8, the lifting means are preferably placed in positions between the central opening 5 and the outer edges 11, for example the positions designated as 6 in FIG. 1. When lifting means 7 are lifted, the mass of debris or refuse 13 is thereby directed towards the center of the top layer 1 whereby it slides towards opening 5. Simultaneously, top layer 1 is moved away from bottom layer 3 and a space 9 is enlarged therebetween. Debris or refuse 13 slides through opening 5 and into space 9. It is within this space 9 that the debris or refuse 13 is contained by the inventive receptacle.

As can be seen from FIG. 5, if the opening 5 is composed of a slot with a lap, the refuse or debris 13 will remain within space 9 even if the lifting means 7 are released and the top layer 1 is allowed move back in a position closer to bottom layer 3.

Figure 6:
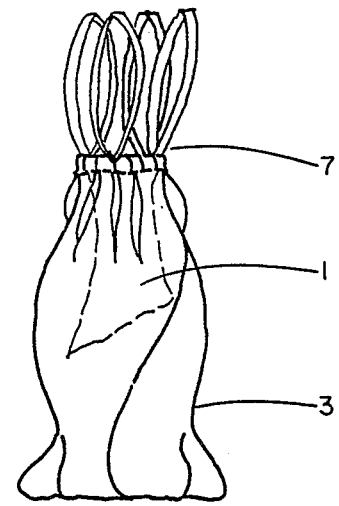

Nevertheless, upon fully lifting lifting means 7, all of the refuse or debris 13 should ultimately fall through opening 5 into space 9 whereupon the lifting means 7 can be brought together and tied as shown in FIG. 6. In this arrangement, the top layer 1 of the convertible receptacle is turned inside the space 9 and only the bottom layer 3 is exposed.

Figure 8:
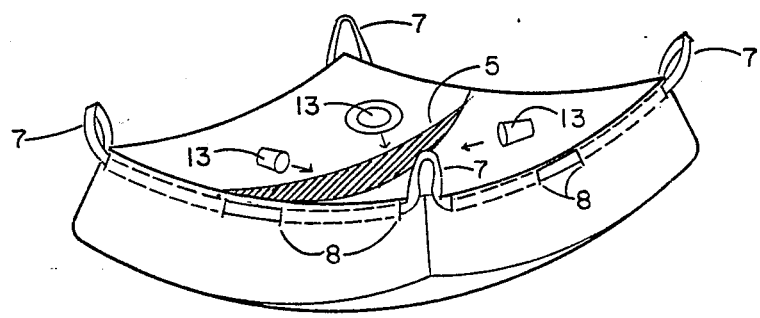
FIG. 8 is a perspective view of the invention showing its conversion from tablecloth into trash bag.

As shown in FIGS. 7 and 8, a further preferred embodiment of the inventive receptacle includes the use a drawstring as lifting means 7. The drawstring may be laced through openings 8 made in the top layer 1 and arranged in a path lying between opening 5 and edge 11. The drawstring may also be applied to the surface of top layer 1, by attaching loops or similar means, which may be economical to manufacture.

Although the invention is shown in an embodiment most suitable for a disposable table cloth, the invention may also be applied as a drop cloth in construction applications or as a leaf bag in gardening applications. The invention can be applied in hospital settings or for clinical use for sanitary disposal, since the waste need not be handled and the top layer folds into the opening and is encompassed by the lower layer.

The invention may be manufactured in various sizes and shaped and can, for example be used as a table cloth for changing a baby's diapers or for any other activity which generates waste needing rapid and sanitary disposal.

The invention has been described as a waste receptacle. However, it can be applied to contain items other than waste. For example, the invention can be used as a convertible beach bag/towel, if constructed of the appropriate materials and dimensions. In general, although the preferred embodiments show the invention converting from sheet material into a bag, the reverse can also be applied. That is, other embodiments within the scope of the appended claims may envision conversion from bag to sheet material, rather than the reverse.

Although the invention is described and illustrated with reference to a plurality of embodiments thereof, it is to be expressly understood that it is in no way limited to the disclosure of such preferred embodiments but is capable of numerous modifications within the scope of the appended claims.

We claim:

1. A convertible receptacle comprising
   an upper and a lower layer of sheet material, said layers having peripheries and being attached to each other at respective peripheries, such that said upper and lower layer may lie adjacent each other on a flat surface;
   said upper layer being provided with a centrally located opening; and
   lifting means, said lifting means attached to said upper layer encompassing said opening and being located between said opening and said periphery;
   such that, upon lifting said lifting means said upper layer is lifted from said lower layer and a receptacle is formed, said receptacle being accessible by way of said central opening;
   whereby objects residing on said upper layer are caused to fall into said opening and then into said receptacle.

2. A convertible receptacle as claimed in claim 1, further comprising
   said lifting comprising drawstring means arranged in a path between said opening and said periphery.

3. A convertible receptacle as claimed in claim 1, wherein said upper layer comprises two parts and said opening comprises an overlapping of said two parts.

4. A convertible receptacle as claimed in claim 1, wherein said upper and lower layers form an interspace which becomes the receptacle when said upper layer is lifted from said lower layer.

5. A convertible receptacle as claimed in claim 1, wherein further lifting of said lifting means causes said receptacle to close.

6. A convertible receptacle as claimed in claim 1, wherein further lifting of said lifting means causes a portion of said upper layer to become encompassed by said receptacle.

7. A convertible receptacle as claimed in claim 4, wherein access to said interspace is solely through said opening.

* * * * *